United States Patent [19]

McAndrew

[11] 4,192,069
[45] Mar. 11, 1980

[54] UTILITY ARCH

[76] Inventor: James R. McAndrew, 3233 S. Sherwood Forest Blvd., Baton Rouge, La. 70816

[21] Appl. No.: 908,724

[22] Filed: May 23, 1978

[51] Int. Cl.² ............................................. A61C 7/00
[52] U.S. Cl. ................................................... 433/21
[58] Field of Search ........................................ 32/14 A

[56] References Cited

U.S. PATENT DOCUMENTS

| 783,609 | 2/1905 | Canning | 32/14 A |
| 3,893,241 | 7/1975 | Moriarty | 32/14 A |

Primary Examiner—Robert Peshock
Attorney, Agent, or Firm—Roy, Kiesel, Patterson & Abadie

[57] ABSTRACT

An improved utility arch utilized in straightening teeth having bendable posts attachable to the buccal bridge section of the arch.

9 Claims, 3 Drawing Figures

UTILITY ARCH

BACKGROUND OF THE INVENTION

1. Field of the Invention

This invention relates generally to dentistry and, more specifically, to improvement in utility arches.

2. Prior Art

The desire for proper positioning of teeth in the mouth cavity has led to the development of a technique called "Light Progressive Technique." Basically, this technique employs certain small forces directionally applied to the teeth. To create these forces, it is presently necessary to employ one of six different designated utility arches, depending upon the tooth movement desired. A description of these various utility arch designs can be found in an article entitled "Biomechanics of the Light Progressive Technique (No. 7)" by Robert M. Ricketts, Ruel W. Bench and James J. Hilgers. Although these arch designs are effective, there is need for a single universal utility arch that can provide a wide range of forces in almost any direction.

SUMMARY OF THE INVENTION

Therefore, it is an object of this invention to provide an improved utility arch for straightening teeth.

Another object of this invention is to provide a universal utility arch.

Still another object of this invention is to provide a utility arch that can be easily adjusted to provide the desired directional pressure against the teeth.

Other objects and advantages of this invention will become apparent from the ensuing descriptions of the invention.

Accordingly, an improved utility arch is provided comprising bendable posts attached to at least one of the buccal bridge sectons of the utility arch.

PREFERRED EMBODIMENT OF THE INVENTION

Figure 1:
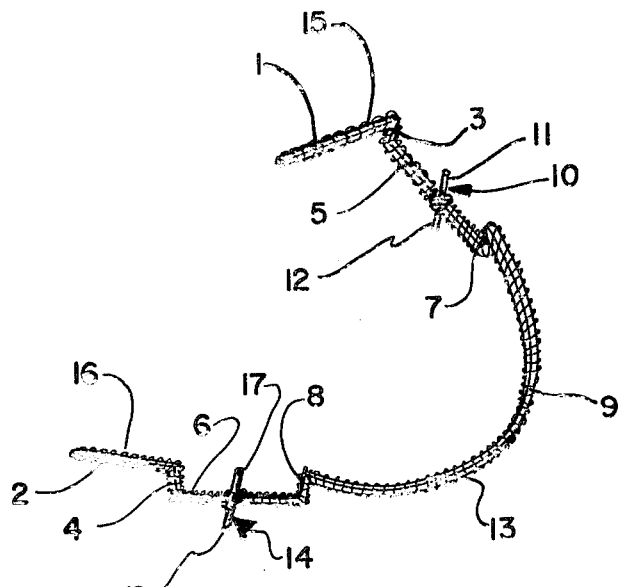
FIG. 1 illustrates one preferred embodiment of the utility arch of this invention.

A conventional utility arch, as well as, the utility arch of this invention is constructed preferably from 0.016×0.016 or 0.019×0.019 size blue Elgiloy wire, having molar sections 1 and 2, posterior vertical step areas 3 and 4, buccal bridge sections 5 and 6, anterior vertical step areas 7 and 8, and anterior section 9.

Now flexible metal post 10, preferably constructed from 0.028 inch diameter brass rod, is soldered or otherwise fixedly attached to buccal bridge section 5 so that ends 11 and 12 extend upward and downward, respectively, from buccal bridge section 5. In a preferred embodiment, center coil spring 13 is slipped onto the arch and positioned between post 10 and post 14 which is soldered or otherwise fixedly attached on buccal bridge section 6 as shown. Finally, posterior coil springs 15 and 16 are positioned on the arch at either end as shown. Preferably, coil springs 13, 15 and 16 will be constructed from 0.006 to 0.0056 inch diameter flexible wire, depending upon the amount of force to be created.

Figure 2A:
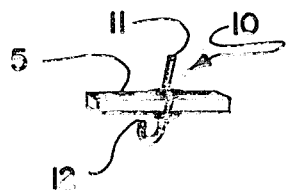
FIG. 2A is an illustration of one post design utilized in accordance with this invention.
Figure 2B:
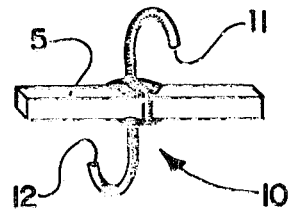
FIG. 2B is an alternate embodiment of a post design utilized in this invention.

As before, post 14 will have ends 17 and 18 which extend above and below, respectively, buccal bridge section 6. Since posts 10 and 14 are constructed from bendable material that can be hand-shaped by pliers as shown in FIGS. 2A and 2B to provide attaching means for rubber bands which are positioned in the mouth cavity and used to apply the proper directional force against the teeth.

There are, of course, many obvious modifications not disclosed in the specific embodiments described but which are intended to be included within the scope of this invention as defined by the following claims.

What I claim is:

1. A utility arch used in straightening teeth constructed from bendable wire and having first and second molar sections, first and second buccal sections and an anterior section, the improvement of which comprises a first post means fixedly attached to said buccal section, second post means fixedly attached to said second buccal section, said first and second post means having ends extending above and below, respectively, said first and second buccal bridge section, and a first coil spring wound around said wire between said first and second post means.

2. A utility arch according to claim 1 wherein both said post means are constructed of a 0.028 inch diameter square brass rod.

3. A utility arch according to claim 1 wherein said first coil spring is constructed from 0.006 to 0.0056 inch diameter flexible wire.

4. A utility arch according to claim 1 wherein a second coil spring is wound around said wire posterior to said first post means and about said first molar section.

5. A utility arch according to claim 1 wherein a third coil spring is wound around said wire posterior to said second post means and about said second molar section.

6. A utility arch according to claim 4 wherein said second coil spring is constructed from 0.006 to 0.0056 inch diameter flexible wire.

7. A utility arch according to claim 5 wherein said third coil spring is constructed from 0.006 to 0.0056 inch diameter flexible wire.

8. A utility arch according to claim 1 wherein said first post means extends above said first buccal bridge section a distance sufficient to be bent.

9. A utility arch according to claim 8 wherein said second post means extends above said second buccal bridge section a distance sufficient to be bent.

* * * * *